United States Patent [19]

Bawa

[11] Patent Number: 5,137,728
[45] Date of Patent: Aug. 11, 1992

[54] OPHTHALMIC ARTICLE

[75] Inventor: Rajan Bawa, Fairport, N.Y.

[73] Assignee: Bausch & Lomb Incorporated, Rochester, N.Y.

[21] Appl. No.: 288,398

[22] Filed: Dec. 22, 1988

Related U.S. Application Data

[63] Continuation of Ser. No. 162,702, Mar. 1, 1988, abandoned.

[51] Int. Cl.⁵ .............................................. A61M 31/00
[52] U.S. Cl. ..................................... 424/427; 424/422; 424/424; 424/428; 424/429
[58] Field of Search .......................... 424/427, 429, 428

[56] References Cited

U.S. PATENT DOCUMENTS

| | | | |
|---|---|---|---|
| 3,828,777 | 8/1974 | Ness | 424/427 |
| 3,986,510 | 10/1976 | Higuchi et al. | 424/428 |
| 4,014,335 | 3/1977 | Arnold | 424/427 |
| 4,668,506 | 5/1987 | Bawa | 424/427 |

Primary Examiner—Thurman K. Page
Assistant Examiner—James M. Spear
Attorney, Agent, or Firm—Salvatore P. Pace; Denis a. Polyn; Craig E. Larson

[57] ABSTRACT

An ocular insert for insertion into the cul de sac of the eye which is a substantially circular disc having a concave posterior surface and a convex anterior surface with a radius of curvature less than that of the sclera and a center thickness of less than about 1.5 mm.

14 Claims, 1 Drawing Sheet

OPHTHALMIC ARTICLE

This application is a continuation in part of the application Ser. No. 07/162702 filed on 03/01/88 now abandoned.

FIELD OF THE INVENTION

This invention relates to an ophthalmic article and, more particularly, to a polymeric ocular insert for therapeutically treating the eye.

BACKGROUND

The use of ocular inserts of various shapes for treating eye disorders is known. For example, the patent to Katz, U.S. Pat. No. 4,343,787, describes the use of a water-soluble polymer to make a device which is inserted under the lower lid of the eye for treating dry eye syndrome. It is said that it can be of any shape and size and, preferably, is in the shape of a rod, doughnut, oval or quarter moon. It can be so large as to cover the entire globe of the eye.

Another ocular insert is suggested by the patent to Ness, U.S. Pat. No. 3,618,604. This is a generally crescent-shaped small article which fits under the lower lid and is used for dispersing drugs to the eye. Still other such articles of various shapes are disclosed in U.S. Pat. Nos. 3,995,635; 3,867,519; 3,828,777; 3,854,480; 4,571,039; 4,484,922; and 4,592,752.

While these disclosed devices may find use for certain purposes, each of them has one or more drawbacks which are particularly related to their shapes. For example, several of the devices are so large that they obscure the vision. Others which are small enough to fit under the lower lid and not obscure the vision, are of non-symmetrical shape and are difficult to place in the eye, perhaps requiring the use of a special implement for placing the device in the eye. Others are uncomfortable to wear. Still others are difficult to retain in the eye and demonstrate a high rate of dislodgement.

BRIEF SUMMARY OF THE INVENTION

The present invention provides a novel ocular insert for treating the eye or for delivering medication to treat the eye. The insert is a substantially circular disc, having a concave posterior and a convex anterior surface. The posterior surface is placed in contact with the sclera of the eye. More specifically, the radius of curvature of the posterior surface of the insert is less than that of the sclera of the eye and the center radius thickness of the insert is less than 1.5mm. The insert may be composed of water-soluble, inert or bioactive, non-cytotoxic material suitable for the treatment of dry eye syndrome or may be a non-soluble, non-cytotoxic polymer which is capable of acting as a drug-releasing matrix.

THE DRAWINGS

The invention will be described in more detail by reference to the drawings of which FIG. 1 is a view of an insert of the invention inserted in the lower cul de sac of an eye;

FIG. 2 is a cross sectional enlarged side view of an insert of the invention; and FIG. 3 is a view of a commercially available state-of-the-art insert.

DETAILED DESCRIPTION

Figure 1:
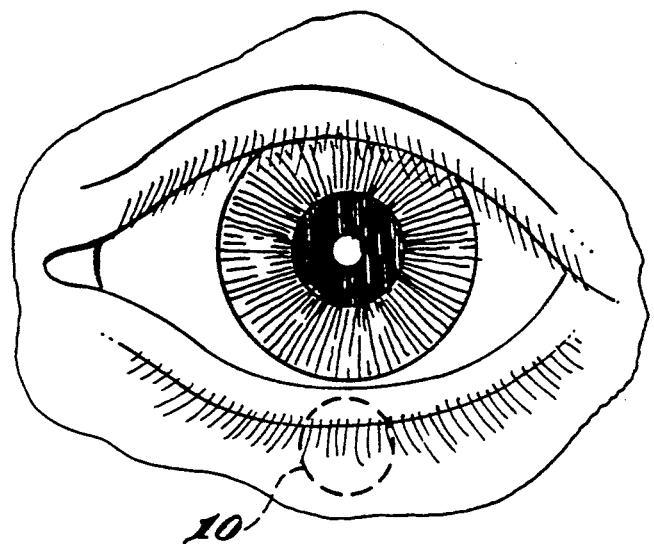

As shown in FIG. 1, the ophthalmic insert of the invention is substantially symmetrical in view. More particularly, it is substantially circular and of small diameter, e.g., of the order of 3 to 6mm and preferably about 3.5 to about 4.5 mm. Being symmetrical in shape, the device is easily placed on the sclera by the wearer's index finger. In this respect, the new device provides a significant advantage over assymmetrical devices such as shown in U.S. Pat. No. 3,618,604 and in other publications. In placing the latter devices in the eye, the patient must carefully insure that the device is correctly aligned for placement in the eye. The insert of the present invention avoids this difficulty. Furthermore, rod-shaped and other irregularly shaped or assymmetrical devices having flat anterior surfaces can be ejected inadvertently from the eye, a problem minimized by the article of the present invention.

As FIG. 1 also shows, the insert 10 of the invention is of such small diameter that it fits under the lower lid or at least below the cornea and does not obscure the vision. Large devices as referred to in U.S. Pat. No. 4,343,787 and other references cited are annoying in this respect. Alternatively, the article may be placed under the upper lid of the eye.

Figure 2:
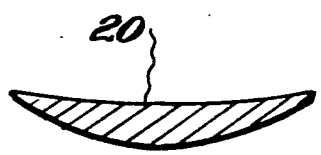
Figure 3:
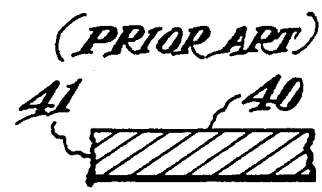

Another important characteristic of the present insert is illustrated by FIG. 2. It has now been found that unlike previously believed, the radius of curvature of the posterior surface of the insert should not have an identical curvature with that of the sclera of the eye. In fact, it has been surprisingly discovered that when the posterior surface has a radius of curvature which is less than that of the sclera of the eye and preferably more than the radius of curvature of the anterior surface, fewer dislodgements result.

The radius of the normal adult sclera is from about 8 to about 14mm and most often about 12mm. The radius of curvature of the posterior surface of the present insert is less than the radius of the sclera of the wearer of the insert and is preferably less than about 10mm in most adults which results in an average ratio of the radius of curvature of the posterior surface to the radius of curvature of the sclera of less than about 0.8. It is also preferred that the radius of curvature of the anterior surface be less than the radius of curvature of the posterior surface. Moreover, the thickness of the insert is less than about 1.5mm and preferably less than about 1.0mm.

It should be recognized that the radius of curvature of any particular sclera will vary from the averages provided above. Moreover, the present invention may be used in pediatric, veterinarian, and other related uses provided the ratio of curvature is about 0.8 as discussed above.

The inserts of the present invention may be formed from non-bioerodible, hydrophilic materials; hydrophobic materials; bioerodible; and biodegradable materials.

"Bioerodible" connotes a water soluble, non-toxic material — a material which dissolves when placed on the eye. Examples are water soluble polymers of cellulose derivatives such as methylcellulose, alkali carboxyloweralkyl cellulose (sodium carboxymethyl cellulose), hydroxyloweralkyl cellulose, (hydroxymethyl cellulose, hydroxyethyl cellulose, hydroxypropyl cellulose), hydroxyloweralkyl-lower alkyl cellulose, (hydroxypropylmethyl cellulose); (Lower alkyl meaning from 1–4 carbon atoms); natural products (natural gums), such as gelatin, metal alginates (Na, K, Ca, Zn, Al), pectins, tragacanth, karaya, chondrus, agar, acacia; the starch derivatives such as hydroxyethyl starch ethers, hydroxypropyl starch; dextran, lower hydroxyalkyl dextran, carboxy-loweralkyl dextran, polyalkylene glycols (polyethylene and polypropylene glycols), as well as other synthetic derivatives such as poly vinylmethyl ether, poly ethylene oxide, neutralized carbopol and xanthan gum, and mixtures of such polymers.

Preferred bioerodible materials are the cellulose derivatives; especially methylcellulose, sodium carboxymethyl cellulose, hydroxyethyl cellulose, hydroxypropyl cellulose, and hydroxypropylmethyl cellulose.

In addition to serving as carriers for ophthalmic medicaments, the bioerodible ocular inserts may also contain buffering agents, and preservatives.

"Biodegradable" connotes materials which undergo hydrolysis of chemical bonds and accordingly undergo a dissolution process. Examples of such materials include polysaccharides, polyanhydrides, collagen, and polyamino acid biopolymers. Further, see U.S. Pat. No. 4,638,045 and *Bioerodible Polyanhydrides as Drug-Carrier Matrices* by K.W. Leong P. D'Amore, M. Marletta and R. Langer, Journal of Biomedical Materials Research, Vol. 20, 51–64 (1986) for additional discussion of bioerodible materials.

The biodegradable ocular inserts of this invention can also contain plasticizers, buffering agents and preservatives. The invention is therefore also directed to compositions containing these materials along with the biodegradable polymer. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from 1 to about 40% by weight. A particularly preferred plasticizer is water which is present in amounts of at least about 5% up to about 40%. In actual practice, a water content of from about 5% to about 20% is preferred since it may be easily accomplished and adds the desired softness and pliability to the insert.

When plasticizing the solid product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 5% to about 20%.

Suitable water soluble preservatives which may be employed in the insert include sodium bisulfite, sodium thiosulfate, ascorbate, benzalkonium chloride, chlorobutanol, thimerosal, phenylmercuric acetate, phenylmercuric borate, parabens, benzyl alcohol, phenylethanol, and polyhexamethylene biguanide. These agents may be present in amounts of from 0.00001 to 5% by weight of solid insert, the amount determined by the preservative employed.

Suitable water soluble buffering agents are alkali, alkali earth carbonates, phosphates, bicarbonates, citrates, borates, and the like, such as sodium phosphate, citrate, borate, acetate, bicarbonate and carbonate. These agents may be present in amounts sufficient to obtain a pH of the system of between 5.5 to 8.0 and especially 7–8; usually up to about 2% by weight of polymer.

Nonbioerodible hydrophilic materials useful in forming the ocular inserts of this invention are exemplified by hydrophilic polymers having an olefinic bond. Included for example are polymers of the hydroxyalkyl esters and amides (both N-substituted and unsubstituted) of aloha-, beta-unsaturated carboxylic acids, N-vinyl lactams and 2-acrylamido-2-methylpropane sulfonic acid. The unsaturated acids usefully employed include acrylic acid, crotonic acid, methacrylic acid, itaconic acid, maleic acid, fumaric acid, and the like. The anhydrides of these acids may also be employed.

Polyfunctional alcohols which form the hydroxy alkyl esters of such acids include glycol, glycerol, propylene glycol, trimethylene glycol, and other polyhydric alkanols, dialkylene glycols of 2 to 12 carbon atoms, polyalkylene glycols, etc. Polyalkylene glycols are exemplified by triethylene glycol, tetraethylene glycol, pentaethylene glycol, hexaethylene glycol, and the like. Presently preferred hydrophilic materials contain hydroxyalkyl esters, especially hydroxyalkyl methacrylate (HEMA).

Useful amides of the unsaturated acids include diacetone acrylamide and N-mono-substituted diacetone acrylamide. Also useful are the amines of the foregoing acids such as mono- or di-alkylamino substituents.

Nitrogen containing monomers which may be used in the preparation of the polymers and copolymers of this invention are conveniently referred to as N-vinyl lactam which includes (a) N-vinyl lactams per se and (b) other heterocyclic N-vinyl monomers. Illustrative of the N-vinyl lactams that are employed in this invention are N-vinyl-2-pyrrolidone, N-vinyl-2-caprolactam and the like which may be substituted in the lactam ring by one or more lower alkyl groups such as methyl, ethyl or propyl, e.g., N-vinyl-5-methyl pyrrididone, N-vinyl-3,3-dimethyl pyrrolidone, N-vinyl-5-ethyl pyrrolidone, N-vinyl-6-methyl piperidone, etc. Illustrative of the other heterocyclic N-vinyl monomers used in preparing the polymers of this invention are N-vinyl imidazole, N-vinyl succinimide, N-vinyl diglycolylimide, N-vinyl glutarimide, N-vinyl-3-morpholinone, N-vinyl-5-methyl-3-morpholinone, etc. The lactams may be effectively employed alone or in admixture with other lactam monomers to give hydrogels having desirable characteristics.

In addition to the hydrophilic monomers described above, other monomers (typically up to 40 wt.%) may be used to form copolymers and tailor the properties of the material to a particular application.

Cross-linking agents can be employed in varying amounts and desirably in an amount from about 3 to about 30 parts by weight of the total monomers present. Examples of cross-linking agents include polyfunctional derivatives of the previously enumerated alpha-, beta-unsaturated acid, e.g., acrylic acid, methacrylic acid, crotonic acid, itaconic acid, maleic acid, and fumaric acid; amides such as acrylamide, methacrylamide; and multi-vinyl and substituted benzenes. More particularly. these cross-linking agents include, but are not limited to, the following: ethylene glycol diacrylate or dimethacrylate, diethylene glycol diacrylate or dimethacrylate, triethylene glycol diacrylate or dimethacrylate, tetraethylene glycol diacrylate or dimethacrylate, polyethylene glycol diacrylate or dimethacrylate, trimethylolpropane triacrylate or trimethacrylate, bisphenol A diacrylate or dimethacrylate, ethoxylated bisphenol A diacrylate or dimethacrylate, pentaerythritol tri- and tetra-acrylate or methacrylate, tetramethylene diacrylate or dimethacrylate, methylene bisacrylamide or methacrylamide, dimethylene bisacrylamide or methacrylamide, N,N'-dihydroxyethylene bisacrylamide or methacrylamide, hexamethylene bisacrylamide or methacrylamide, decamethylene bisacrylamide or methacrylamide, divinyl benzene, vinyl methacrylate, allyl methacrylate, etc. A preferred cross-linking agent is allyl methacrylate.

Still other useful cross-linking agents include 1,3-bis (4-methacryloyl oxyalkyl) tetra disiloxane and similar poly (organo-siloxane) monomers set forth in U.S. Pat. No. 4,153,641. Another group of useful cross-linking agents are the resonance free di(alkylene tertiary amine) cyclic compounds, e.g., N,N'-divinyl ethylene urea, as disclosed in U.S. Pat. No. 4,436,887. Yet another group are di- or polyvinyl ethers of di- or polyvalent alcohols such as ethylene glycol divinyl ether.

A further example of additional monomeric components usefully incorporated into the hydrophilic material is alpha-, beta-unsaturated carbonyl modified or unmodified amino acid monomer or monomers. This component can be present in varying amounts, desirably in an amount from about 5% to 27% w/w and, more preferably, about 6% w/w of the total monomers present in the polymerization mixture. The modified or unmodified amino acid monomers are hydrophilic compounds which contribute significantly to the swelling of the polymer in water and permit higher oxygen diffusion.

The alpha-, beta-unsaturated carbonyl modifier for the modified amino acids of this invention may be, for example, acrylic acid, crotonic acid, methacrylic acid, maleic acid, fumaric acid, itaconic acid and their functional derivatives, e.g., acid chlorides, anhydrides, amides and esters. The more preferred modifiers are methacrylic acid and methacryloyl chloride.

An amino acid is an organic acid whose molecule contains both a carboxyl group (COOH) and an amino group ($NH_2$) coupled with an alkyl, cycloalkyl, aryl or heterocyclic structure, the alkyl, cycloalkyl or heterocyclic structure being free of olefinic unsaturation. The alpha-, beta-carbonyl substituent can be attached to either the amino group or the hydroxy group of the amino acid, depending on the structure of the amino acid. Additionally, the carbonyl substituent can attach to other reactive groups, if present, in the amino acid, e.g., thiol (SH) or phenolic hydroxyl.

Amino acids useful in the preparation of the modified acids of this invention include, but are not limited to, beta-alanine, gamma-aminobutyric acid, omega-aminocaproic acid, omega-aminododecanoic acid, beta-cycanoalanine, epsilon-methylhistidine, canavanine, djenkolic acid, 1-azaserine, gamma-methylene glutamic acid, N-methyltyrosine, glycine, alanine, serine, cystine, cysteine, lanthionine, phenylalanine, tyrosine, diiodotyrosine, tryptophan, histidine, aminobutyric acid, methionine, valine, norvaline, leucine, isoleucine, norleucine, arginine, ornithine, lysine, aspartic acid, glutamic acid, threonine, hydroxyglutamic acid, proline, hydroxyproline, asparagine, glutamine, desmosine, isodesmosine, 5-hydroxylysine and the like. Preferred amino acids are glycine, glutamic acid, desmosine and isodesmosine.

Hydrophilic materials may also contain a lower alkyl (C1-C4), polar solvent, especially when amino acid comonomers are employed. The solvent is preferably volatile, demonstrating high water solubility parameters such as a lower alkyl (C1-C4) alcohol, an unmodified or modified ketone and the like for controlling the viscosity of the polymer. Suitable solvents may also include mixtures of modified and unmodified ketones in any proportions and mixtures of a lower alkyl (C1-C4) alcohol and water in any proportions. Examples of solvents are methanol, ethanol, propanol, butanol, isopropanol, acetone, methyl ethyl ketone, hydroxyacetone, etc. Typically, equal parts of solvent and linear, polymerized polymer are used in the preparation of the formulation. However, different amounts of the solvent may be used with the polymer though generally less conveniently. When this process is followed, a residue of the solvent remains in the formulation in varying amounts depending upon reaction conditions such as time and temperature.

Optionally, a chain regulator or chain transfer agent may be added if a particular monomer-solvent combination requires it. For example, certain combinations containing solvents such as butanol may require large quantities of butanol which may not be desirable in the product. If a chain regulator is added, a smaller amount of butanol may be used.

For some applications the polymerizates formed from hydrophilic monomer(s) may lack the desired physical handling properties. It is another aspect of this invention in such circumstances to incorporate one or more hydrophobic monomers in the above polymers in varying amounts, desirably from about 8% to about 20% w/w of the total monomers present. Among other things, the hydrophobic monomers are useful as modulus modifiers.

The modulus modifier may be, for example, cycloalkyl ester, tertiary-butyl styrene, polycyclic acrylate or methacrylate, and the like as well as mixtures thereof. More particularly the polycyclic modifiers may be isobornyl acrylate, isobornyl methacrylate, dicyclopentanedienyl acrylate, dicyclopentanedienyl methacrylate, adamantyl acrylate, adamantyl methacrylate, isopinocamphyl acrylate, isopinocamphyl methacrylate, etc. and mixtures thereof. Illustrative of these cycloalkyl modifiers are menthyl methacrylate, menthyl acrylate, tertiarybutyl cyclohexyl methacrylate, isohexyl cyclopentyl acrylate, methylisopentyl cyclooctyl acrylate and the like.

In addition to the modulus modifiers other well known hydrophobic monomers may be used in the formulation of the polymers and copolymers of this invention to further tailor the properties to the particular application. The hydrophobic monomers of this invention include monomers which contain at least one silicon or fluorine atom as a part of its composition. Hydrophobic monomers include alkyl, cyclo-alkyl and aryl acrylates and methacrylates as well as mono- or disubstituted itaconates, styrene and its derivatives, acrylonitrile, vinyl esters such as vinyl acetate or vinyl, pentacetyl gluconate, vinyl ethers such as vinyl butyl ether, allyl esters such as allyl acetate, propionate or butyrate, fluorine containing monomers such as octafluoropentyl methacrylate and silicon containing monomers, e.g., 1,1,1-tris (trimethoxysiloxy)-3-methacryloxypropylsilane or heptamethyltrisiloxanyl ethyl acrylate.

The monomeric mixtures, comprising the hydrophilic monomer(s), the modified or unmodified amino acid monomer(s), the optional hydrophobic monomer(s), the cross-linking agent, the lower alkyl (C1-C4) alcohol and the optional chain regulator are generally clear, colorless liquids of varying viscosity. These monomer mixtures are polymerized but not cross-linked using ultraviolet light at room temperature. Medicinal agent may be dissolved in this linear, polymerized polymer that can then be cross-linked by ultraviolet light and/or heat. Before cross-linking takes place, the linear polymer is characterized by being soluble in methanol and isopropanol. After cross-linking, an insoluble polymer is formed.

As catalysts for carrying out the polymerization, there may be employed a free radical catalyst (initiator) in varying amounts and typically in the ran9e of about 0.05% to 3% w/w of the polymerizable monomer mixture. The preferred amount of catalyst is 0.1% to 2.5% w/w of the total monomers present. Usually, the catalyst is added initially to the monomers and then the polymerization procedure is completed. The free radical type initiators suitable for this invention are well known in the art.

One preferred process for preparing the sustained-release hydrophilic polymeric hydrogel dosage is to dissolve a medicinal agent directly into the linear polymer. The drug becomes intimately mixed in the polymeric matrix rather than remaining as particulate matter. Subsequent cross-linking prevents chemical bonding of the drug with the polymer allowing for greater recovery of the drug upon tissue contact. The drug would release slowly into the tissue for local or systemic effect over prolonged time intervals at lower concentrations thereby eliminating or reducing side effects. The amount of the drug used in the preparation of the dosage forms will vary depending upon the physicochemical properties of the selected drug and the therapeutic effect desired to be achieved. Typically, the drug is added on an equivalency basis, that is, an equivalent for equivalent basis of drug to the linear, polymerized polymer. Although a stoichiometric number of equivalents of drug and the linear, polymerized polymer is preferred, other amounts can also be used. As an example of pilocarpine hydrochloride, varying concentrations of the compound may be employed, desirably an amount from about 5% to about 15% w/w, of pilocarpine hydrochloride to the weight of the linear polymer, and preferably 9.1% w/w, for incorporation in the dosage form.

The polymeric composition provides appreciable time release of the medicament. The release rate of a drug from the polymeric matrix varies with cross-linking density and type of polymer barrier system. Additionally, the release rate depends upon the viscosity of the linear, uncross-linked polymer which may be controlled by the addition of a polar, volatile solvent such as a lower alkyl (C1-C4) alcohol.

Nonbioerodible hydrophobic materials useful in forming the ocular inserts of this invention are exemplified by the "modulus modifiers" described above in connection with the description of nonbioerodible hydrophilic materials. Hydrophilic materials are typically copolymers prepared from monomeric mixtures containing more than about 60 parts by weight of hydrophilic monomers; hydrophobic materials, by contrast, are typically copolymers prepared from monomeric mixtures containing more than about 60 parts by weight of hydrophobic monomers.

The hydrophobic polymeric materials may be cross-linked as previously discussed for hydrophilic materials to modify physical handling properties. Other optional additives include inhibitors and stabilizers. Polymerization is performed according to techniques well known in the art.

Medicinal agents may desirably be incorporated into any of the materials used to form the the ocular inserts of this invention. A variety of processes may be used to prepare sustained-release polymeric dosage forms whereby a medicinal agent is retained by the hydrophobic polymeric matrix and, upon tissue contact, is gradually released into the tissue. One process comprises incorporating the medicament directly into the monomer mixture and polymerizing the monomers in the presence of the drug to make a single layer of polymer plus drug as the dosage form. Another process uses the drug-polymer layer as a middle layer in a "sandwich" dosage form in which two drug-free polymer layers are formed on either side of the middle layer containing the drug. Alternatively, a two layer system may be formed having one layer as polymer plus drug and the other layer as drug-free polymer. In any of the above methods of preparation, the medicament is incorporated as a suspension of drug particles in the hydrophobic monomer solution mix. The amount of the drug used in the preparation of these dosage forms will vary depending upon the physicochemical properties of the selected drug and the therapeutic effect desired to be achieved. As an example of pilocarpine hydrochloride, varying concentrations of the compound may be employed, desirably an amount from about 0.1% to about 50% w/w, and preferably 10% w/w, for incorporation in the dosage form of choice.

Regardless of the exact mode of preparation, the hydrophobic polymeric composition provides appreciable time release of the medicament. The release rate varies with cross-linking density, type of polymer barrier system and mode of preparation. For example, a layering technique where only a middle layer contains polymer plus drug may provide a slower release profile than a single layer of polymer plus drug.

The term "a medicinal agent" means a substance used in treating or ameliorating a disease or medical condition. Examples of medicinal agents include, but are not limited to, antibiotics, antivirals, anti-inflammatories, steroids, peptides, polypeptides, cardiotonics, antihypertensives, antiallergies, alpha- and beta-adrenergic blocking agents, anticataract agents, ophthalmic medicaments, ophthalmic lubricating agents, ophthalmic topical or regional anesthetic agents, etc. The ophthalmic medicaments or other medical agents encompass such drugs as pilocarpine, idoxuridine, carbachol, bethanechol, timolol, tetracycline, epinephrine, phenylephrine, eserine, phospholine, demecarium, cyclopentolate, homatropine, scopolamine, nitroglycerin, chlortetracycline, chloramphenicol, gentamycin, penicillin, erythromycin, sulfacetamide, polymyxin B, tobramycin, isofluorophate, fluorometholone, dexamethasone, hydrocortisone, fluorocinolone, medrysone, prednisolone, methyl prednisolone, betamethasone, triamcinolone, interferon, cromolyn, all-trans-retinoic acid (Vitamin A), the nontoxic, pharmaceutically acceptable salts thereof and the like. The category of ophthalmic lubricating agents refers to those agents capable of increasing tear viscosity and retarding water evaporation and includes, for example, polyvinyl alcohol, cellulose polymers such as hydroxypropyl methyl cellulose, a polylactam such as polyvinylpyrrolidone, polyethylene glycol. The topical or regional anesthetic agents, which may be useful during ophthalmic surgery or other ophthalmic procedures, include lidocaine, cocaine, benoxinate, dibucaine, proparacaine, tetracaine, etidocaine, procaine, hexylcaine, bupivacaine, mepivacaine, prilocaine, chloroprocaine, etc.

The term "pharmaceutically acceptable salt" refers to those salts of the parent compound which do not significantly or adversely affect the pharmaceutical properties (e.g., toxicity, efficacy, etc.) of the parent compound. The salts of the present invention which are pharmaceutically acceptable include, for example, chloride, iodide, bromide, hydrochloride, acetate, nitrate, stearate, phosphate, sulfate, etc.

The ocular inserts of this invention may be formed by any of the molding, casting, and/or lathing techniques well known in the art. Preferably the inserts are formed so that they are smooth and do not have sharp edges or corners which could irritate or damage the eye.

The following examples demonstrate certain aspects of the present invention. However, it is to be understood that these examples are for illustrative purposes only and do not purport to be wholly definitive as to conditions and scope of this invention.

EXAMPLE 1

A solution was prepared by mixing together 79.1 grams of alpha, omega-bis(4-methacryloxybutyl) poly-dimethylsiloxane, 16.7 grams of methacryloxypropyl tris(trimethylsiloxy) silane, 4.2 grams of methacrylic acid, 0.1 grams of benzoin methyl ether, and 1.0% of a peroxide initiator (LUPERSOL 225 obtained from Pennwalt). To 7.0 grams of the silicone monomer mix was added 3.0 of sieved gentamicin sulphate. This mixture was stirred to obtain a uniform dispersion.

Ten microliters of the dispersion were injected into female molds which were then capped with male molds. The mixture was then cured by ultraviolet light at 70° C. under nitrogen for 1 hour.

The finished insert had a base curve (posterior surface) radius of 10mm, a front curve (anterior surface) radius of 3.5mm, a center thickness of 0.8mm, and a face diameter of 4mm.

The inserts were hydrated for 30 minutes in isotonic buffered saline and placed under the lower eyelid of albino rabbits. Gentamicin levels in the tears were found to gradually decline from a high of about 1800ppm at 5 hours (after installation) to about 40ppm at 330 hours.

EXAMPLES 2-8

Several inserts were prepared having the parameters shown in Table I using the following technique. A clear, homogeneous methacrylate ("HEMA"), 14.9 grams of glycerine, and 0.34 grams of ethylene glycol dimethacrylate. To the mixture is added 0.17 grams of benzoin methyl ether and the mixture stirred to obtain a uniform solution. The mixture was polymerized under cool ultraviolet light for 20 minutes against a suitable optical mold under an inert atmosphere. The back surface of the button so formed was lathed to obtain the parameters shown in Table I.

The inserts were tested with twenty patients for displacements and dislodgements. Accordingly, the inserts were placed in the central inferior cul-de-sac of one of the patient's eyes (selected at random) with the posterior surface touching the scleral conjunctiva. Placement of the insert was accomplished by pulling the patent's lower lid away from the eye; having the patient look superiorly; placing the insert in the now exposed cul-de-sac; having the patient look inferiorly; and then releasing the lower eyelid. The inserts were monitored for the number of displacements (movement of insert within eye) and dislodgements (loss of insert from the eye). The maximum number of displacements or dislodgements recorded for any single patient was three. Removal of the insert was accomplished by manipulating it into the interpalpebral space and either removing it with a modified suction cup (cut down in diameter to match the insert) or using the two-lid rigid lens removal technique.

The results as shown in Table I, demonstrate that the total number of dislodgements decrease as the radius of curvature of the posterior surface of the insert is decreased below that of the sclera (typically about 12mm in the normal adult) providing that the center thickness is less than about 1.0mm. Moreover, the rate of dislodgement is also decreased when the radius of curvature of the anterior surface is less than that of the posterior surface.

TABLE I

| EXAMPLE | 2 | 3 | 4 | 5 | 6 | 7 | 8 |
|---|---|---|---|---|---|---|---|
| Diameter (mm) | 4.5 | 4.5 | 4.5 | 4.5 | 4.5 | 4.5 | 4.5 |
| Thickness (mm) | 0.8 | 0.8 | 0.8 | 0.8 | 1.5 | 0.8 | 0.8 |
| Anterior Radius (mm) | 3.5 | 3.5 | 3.5 | 3.5 | 3.5 | 7.94 | 7.94 |
| Posterior Radius (mm) | 12.0 | 10.0 | 8.0 | 8.0 | 10.0 | 8.0 | 12.0 |
| Displacements* | 5 | 6 | 9 | 7 | 10 | 4 | 9 |
| Dislodgements* | 3 | 2 | 0 | 0 | 6 | 2 | 3 |

*The maximum displacements or dislodgements was recorded for any single patient was three.

What is claimed is:

1. An ocular insert for use behind an eyelid, comprising a substantially circular disc having a concave posterior surface and a convex anterior surface wherein the radius of curvature of said posterior surface is less than the radius of curvature of the sclera of the eye, the center thickness of said insert is less than about 1.5mm and the ratio of the radius of curvature of said posterior surface to the radius of curvature of the sclera is less than about 0.8mm wherein incorporated in said ocular insert a medicinal agent is incorporated therein.

2. An ocular insert capable of dispensing a medicinal agent directly to the eye comprising a substantially circular disc having a concave posterior surface for placement in contact with the sclera of the eye and a convex anterior surface for placement in contact with an eyelid and wherein the radius of curvature of said osterior surface is less than the radius of curvature of the sclera, the center thickness of said insert is less than about 1.5mm, and the ratio of the curvature of said posterior concave surface to the radius of curvature of the sclera is less than about 0.8mm.

3. The insert of claim 1 wherein the radius of curvature of said anterior surface is less than the radius of curvature of said posterior surface.

4. The insert of claim 1 wherein the thickness of said insert is less than about 1mm.

5. The insert of claim 1 wherein he diameter of said insert is between about 3 to about 6mm.

6. The insert of claim 1 wherein said insert is formed from materials selected from non-bioerodible hydrophilic, hydrophobic, bioerodible and biodegradable materials.

7. The insert of claim 6 wherein said insert is formed from bioerodible, biodegradable or non-bioerodible hydrophilic materials.

8. The insert of claim 2 wherein the radius of curvature of said anterior surface is less than the radius of curvature of said posterior surface.

9. The insert of claim 8 wherein said insert comprises a polymeric material.

10. The insert of claim 9 wherein the diameter is about 3.5 to about 4.5mm.

11. The insert of claim 9 wherein the thickness of said insert is less than about 1 mm.

12. The insert of claim 9 wherein said insert is formed from non-bioerodible materials.

13. The insert of claim 12 wherein said insert is formed from materials containing hydroxyalkyl esters.

14. The insert of claim 9 wherein said insert is formed from hydrophobic materials.

* * * * *

UNITED STATES PATENT AND TRADEMARK OFFICE
CERTIFICATE OF CORRECTION

PATENT NO. : 5,137,728
DATED : August 11, 1992
INVENTOR(S) : Rajan Bawa

It is certified that error appears in the above-indentified patent and that said Letters Patent is hereby corrected as shown below:

Column 3, lines 15 and 16, insert --such ophthalmically acceptable addenda as plasticizers -- after "contain".

Column 4, line 8, replace "aloha" with --alpha--.

Column 4, line 34, insert --N-(1-methyl vinyl) pyrrolidone, N-vinyl-2-piperidone-- after "N-vinyl-2-pyrrolidone".

Column 4, line 37, replace "pyrrididone" with --pyrrolidone--.

Column 4, line 60, replace "." with --,--.

Column 6, line 56, delete "," after "vinyl".

Column 7, line 11, replace "ran9e" with --range--.

Column 9, line 31, insert --grams-- after "3.0".

Column 9, line 51, insert --solution is prepared by mixing 85.6 grams of 2-hydroxyethyl-- after "homogeneous".

Column 10, line 50, replace "osterior" with --posterior--.

Column 10, line 58, replace "1" with --3--.

UNITED STATES PATENT AND TRADEMARK OFFICE
CERTIFICATE OF CORRECTION

PATENT NO. : 5,137,728
DATED : August 11, 1992
INVENTOR(S) : Rajan Bawa

It is certified that error appears in the above-indentified patent and that said Letters Patent is hereby corrected as shown below:

Column 12, line 4, insert --hydrophilic-- after "non-bioerodible".

Signed and Sealed this

Twenty-third Day of November, 1993

Attest:

BRUCE LEHMAN

*Attesting Officer*      *Commissioner of Patents and Trademarks*